United States Patent
Richeda

[11] Patent Number: 5,816,815
[45] Date of Patent: Oct. 6, 1998

[54] DENTAL POST AND PIN REPAIR

[76] Inventor: Fred A. Richeda, 11720 Old Ballas Rd., Creve Coeur, Mo. 63141

[21] Appl. No.: 542,916
[22] Filed: Oct. 13, 1995
[51] Int. Cl.$^6$ ..................................................... A61C 5/08
[52] U.S. Cl. ............................................................. 433/220
[58] Field of Search ..................................... 433/220, 221, 433/225

[56] References Cited

U.S. PATENT DOCUMENTS

| | | | |
|---|---|---|---|
| 3,629,943 | 12/1971 | Gindea | 433/220 |
| 4,239,489 | 12/1980 | Ellman et al. | 433/220 |
| 4,622,012 | 11/1986 | Smoler | 433/221 |
| 4,824,371 | 4/1989 | Deutsch et al. | 433/189 |
| 4,846,685 | 7/1989 | Martin | 433/221 |
| 5,104,321 | 4/1992 | Filhol | 433/221 |

FOREIGN PATENT DOCUMENTS

| | | | |
|---|---|---|---|
| 3512938 | 10/1986 | Germany | 433/225 |
| 1498485 | 8/1989 | U.S.S.R. | 433/220 |

*Primary Examiner*—Cary E. O'Connor
*Attorney, Agent, or Firm*—Paul M. Denk

[57] ABSTRACT

A post and pin placed in a radicular or root portion of a tooth as well as in the dentin of fractured or badly broken-down vital teeth to facilitate the distribution of stress throughout the roots and provide structure to support repair parts to restore teeth to a natural shape. Dentistically repair is a method for creating a reservoir space in a tooth to receive a composite resin as well as a stainless steel wire and sleeve components to attach and support a tooth repair part for restorations of a fracture or broken tooth chewing surface. The repair components provide a utilitarian structure of a unique nature.

6 Claims, 1 Drawing Sheet

DENTAL POST AND PIN REPAIR

BACKGROUND OF THE INVENTION

This invention relates to a dental post and pin assembly for anchoring dental repair super structures, such as crowns and veneers, onto a tooth, and a method for effecting permanent installation of the pin.

The prior art has presented a wide variety of structures for the repair and reconstruction of broken or mutilated teeth. In this category of dental repair, the reconstruction of a tooth has required an expensive anchoring pin to make the reconstruction successful. Pin anchors must be carefully shaped and located so the reconstruction installation can be reasonably free of stress and can properly align with adjacent teeth. The problem with such approaches for reconstruction of a broken or mutilated tooth becomes impractical because of space limitations and unnatural alignment with adjacent teeth.

In the category of dental pins of the threaded variety, the problem is related to the extreme care needed to be exercised to prevent the entrance of impurities. Furthermore, threaded type pins are small and difficult to handle. Contoured parts fall into this category of dental repair devices. Stress caused by insertion of the threaded pin is the greatest problem.

SUMMARY OF THE INVENTION

An important object of the invention is to provide post and core pins suitable for applications in the radicular portion of a tooth as well as placement in the dentin of badly mutilated teeth so that the vertical distribution of stress is facilitated in the root whereby proper support is obtained for the reconstruction.

A further object of the invention is to provide a combination of a sleeve to receive an anchor wire set in a composite material reservoir and shaped to allow for correct placement of the sleeve and wire, and assuring the union of the combination to obtain natural distribution of stress through the root.

Another object is to employ a sleeve in a prepared hole in a tooth so the composite material when properly in place can develop the required strength for the repair.

A further object is to locate a sleeve within a prepared hole in a tooth, with the sleeve having predesigned apertures provided therethrough, so that composite material when forced into the sleeve, can surround the anchor wire and pin and exude into the space between the sleeve and the tooth aperture so as to provide greatly enhanced strength for support of the pin in place for holding a crown, or bridge structurally and firmly in place.

Still another object is to rely on a wire post that can be shaped and acid-etched so the full holding area of the wire could become available.

Other objects of the invention will be disclosed in connection with the best mode of the invention to be disclosed hereinafter.

BRIEF DESCRIPTION OF THE EMBODIMENT

Figure 1:
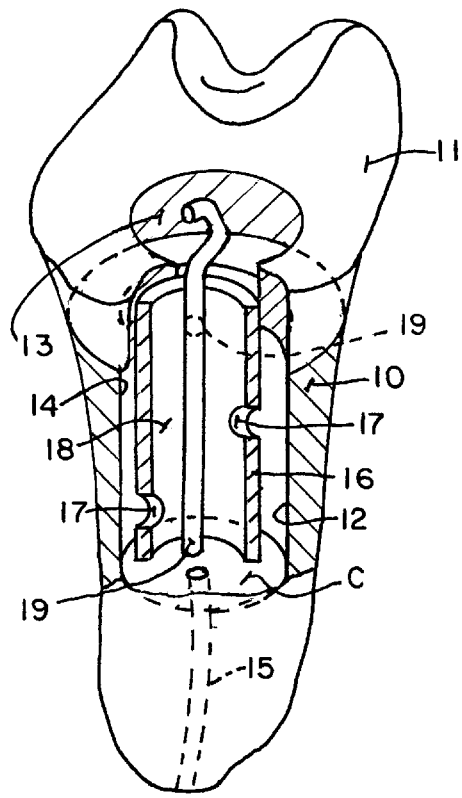
FIG. 1 is a perspective view of a tooth with portions cut away to reveal the components to secure a crown repair on that tooth.

In a dental repair on a tooth 10 needing a crown 11 as a replacement for a natural crown that has been mutilated, the view of FIG. 1 has been disclosed with the side wall cut away at 12 to better explain the endodontic repair work performed on the tooth 10. As depicted, the top surface 13 of the tooth 10 has been cleaned or ground off and a hole 14 is formed in the central area of the tooth above the root canal 15. That hole receives a metal sleeve 16 which has been provided with access ports 17 distributed around and along the sleeve. Those ports open to an annular space 18 defined by the sleeve surrounding the steel wire or pin 19, and a composition C is deposited in a timely manner and is placed inside and outside the sleeve 16.

That composition is a resin having the desired butting or sealing properties which intuitively adheres to the acid etched surface of the sleeve 16 and the wire 19, as well as the dentin wall of the hole 14. The acid etch is generally phosphoric acid, and the resin composition is an oligomes of which the most common are Bis-GMA, urethane-diacrylates, and modified Bis-GMA without the hydroxy groups. Such composition can be obtained from Western Dental Specialties, of San Diego, Calif. The compositions are cured either with chemical activation or by light. It is important that the composites have a flow characteristic that readily wets the surfaces of the dentine, sleeve and wire post, and can migrate under pressure, through the ports or apertures 17 to completely envelop the said sleeve.

Figure 2:
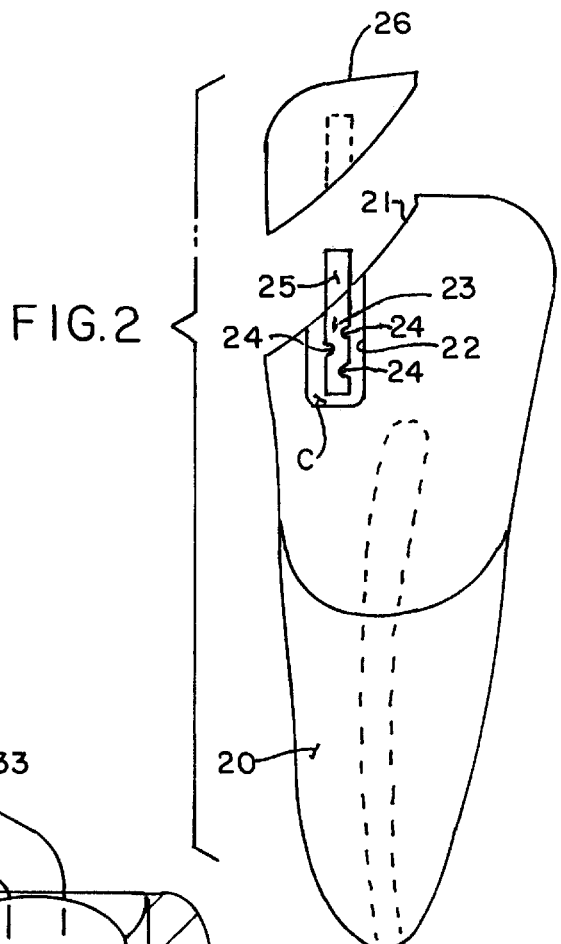
FIG. 2 is a repair of a tooth having a wire or pin implanted to hold a repair thereto.

FIG. 2 is a view of a tooth 20 that needs to be repaired by restoration of a surface or edge fracture 21. In this situation the fracture at 21 has exposed a small part of the tooth 20. The exposed surface is prepared with a shallow hole 22 for the reception of a post 23 formed with side indentations 24 which are positioned in the hole 22. A composition C, as before defined, is placed in the hole 22 so all surfaces of the same and the wire 23 are wetted. Once the post has been set in place, the exposed end 25 is ready to receive the replacement element 26 to repair the fracture and restore the tooth to its natural shape.

Figures 3, 4:
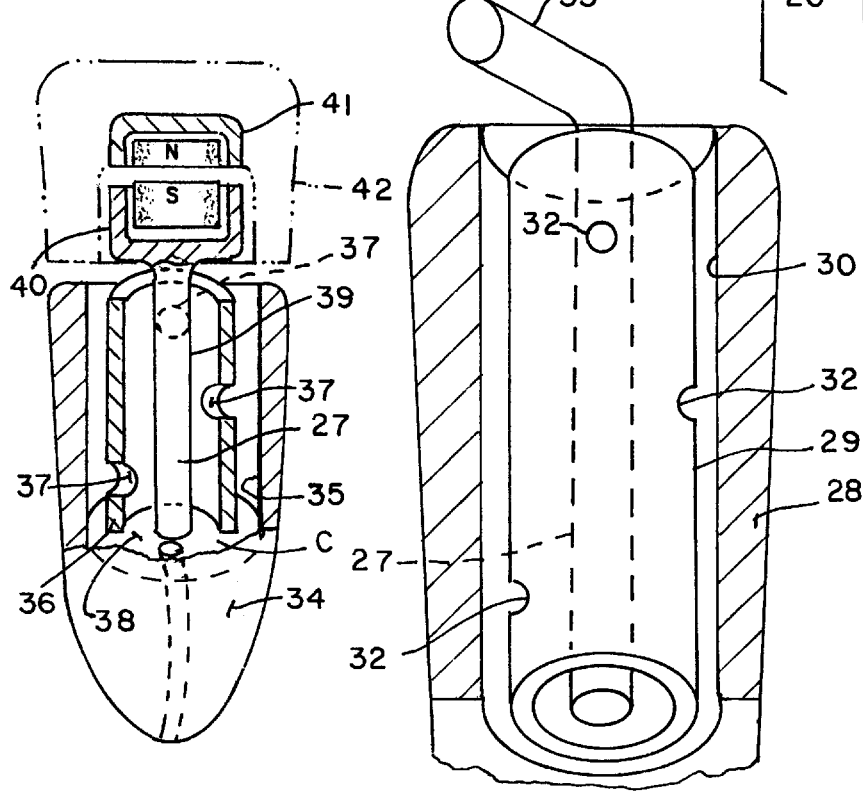
FIG. 3 is a schematic view of a wire or pin implanted post.
FIG. 4 is a tooth repair utilizing a wire post or pin combined with a magnetic steel device.

FIG. 3 is a schematic view in section of a wire post 27 implanted in a tooth 28 by the combination of a metal sleeve 29 set in a hole 30 in the tooth denture which make up the hard calcareous tissue of the tooth 28. The sleeve 29 is formed with apertures 32 distributed around and along the sleeve 29 to receive a composite (not shown) which engages around and inside the sleeve 29. The view of this sketch illustrates that the exposed end portion 33 can be bent, or may be shaped as desired.

In the formation of these sleeves, and the arrangement of their apertures 32, or 17 as shown in FIG. 1, preferably three apertures are arranged along the length of the sleeve, they are located approximately 1200 apart, and approximately 2 mm, in height, away from each other. The initial aperture, are the upper aperture 32, as shown in FIG. 3, is arranged approximately 1 mm below the top of the shown sleeve 29.

FIG. 4 is a special example of a tooth repair in which a magnet receptacle for overdentures is an application that revolutionizes the use of magnets for stabilization of overdentures, or bridgework. The tooth 34 in this case has a hole 35 to receive a sleeve 36 formed with apertures 37 to place the inner and outer sleeve surfaces in communications to receive a composite (not shown) in space 38 to thoroughly seal in the sleeve 36 and metal post 27. The technique for placing the magnetic receptacle 40 is similar to the placing of a post 19 or 23 so the receptacle 40 is properly aligned with other teeth. The magnetic receptacle 40 is integrally formed or applied to the top 39 of the shown post 27. The denture element 41 is placed in the denture 42 on the underside and luted or sealed in. The magnetic pole pieces N and S are placed in the receptacles 40 and 41 so the denture 42 can be luted to the body of the tooth 34. Extra portions of lute may be required. The ease with which magnetic means can be placed, along with its great retentive power, distinguishes this treatment.

Throughout the foregoing description, it is to be understood that stainless steel must be employed wherever metal is referred to. The luting or sealing composition is set forth as being the most desirable. The stainless steel wire is preferred as it restores fractured teeth that are stress free. The formation of holes can be easily accomplished with twist drills, and the pin can be adjusted by snipping as required, using wire cutters, and the exposed end that is exposed can be adjusted with pliers. Proper wetting contact with the composition C can be obtained with acid etching or chemically curved composite placed on the wire. The final step is curing of the composite C.

Variations or modifications to the disclosed subject matter of the invention may occur to those skilled in the art. Such variations or modifications are intended to be included within the scope of the defined invention, and encompassed within the claims of any patent issuing hereon.

Having thus described the invention, what is claimed and desired to be secured by letters patent is:

1. A method for effecting the repair of a fractured tooth wherein a fractured part of the tooth has separated from the tooth itself, and a reservoir space is created at the location of the tooth fracture at the location of repair, the method comprising:

introducing a composite resin into the reservoir space of the tooth;

locating a post in the reservoir space to be wetted by the composite resin;

setting the fractured part of the tooth into position on the post to match the natural tooth; and curing the composite resin to secure the tooth repair fractured part to the post and to hold it onto the natural tooth.

2. The method set forth in claim 1 wherein a series of holes are formed in the post to provide for locating of the composite resin therein.

3. The method set forth in claim 1 including a step of applying to the surface of the tooth fracture and the post an acid to increase the contact surface area of the post and the walls of the reservoir space to the tooth being repaired.

4. The method set forth in claim 3 wherein the step of applying of an acid comprises applying a phosphoric acid on the tooth fracture surface and the post surface to unify the fracture repair part with the natural tooth.

5. The method set forth in claim 1 including a step of setting a sleeve in place to receive the said post, and forming a hook on the post to engage the tooth fracture repair part, said sleeve having a channel therethrough, and said sleeve having a series of apertures therein.

6. The method set forth in claim 1 wherein the step of setting the fractured part of the tooth into position includes magnetically applying a tooth fracture repair part to the post located in the composite resin to effect a tooth repair.

* * * * *